US012779103B2

(12) United States Patent
DePierro

(10) Patent No.: US 12,779,103 B2
(45) Date of Patent: Nov. 3, 2026

(54) SYSTEMS AND DEVICES FOR MONITORING NEGATIVE PRESSURE DEVICES

(71) Applicant: SafeHeal SAS, Paris (FR)

(72) Inventor: Scott DePierro, Madison, CT (US)

(73) Assignee: SafeHeal SAS, Paris (FR)

( * ) Notice: Subject to any disclaimer, the term of this patent is extended or adjusted under 35 U.S.C. 154(b) by 1 day.

(21) Appl. No.: 17/730,125

(22) Filed: Apr. 26, 2022

(65) Prior Publication Data

US 2022/0355017 A1 Nov. 10, 2022

Related U.S. Application Data

(60) Provisional application No. 63/184,360, filed on May 5, 2021.

(51) Int. Cl.
*A61M 1/00* (2006.01)

(52) U.S. Cl.
CPC .............. *A61M 1/73* (2021.05); *A61M 1/604* (2021.05); *A61M 2205/18* (2013.01); *A61M 2210/1064* (2013.01)

(58) Field of Classification Search
CPC .... A61M 1/73; A61M 1/604; A61M 2205/18; A61M 2210/1064; A61M 1/84; A61B 17/1114; A61F 2/04; A61F 5/0076
See application file for complete search history.

(56) References Cited

U.S. PATENT DOCUMENTS 2,821,190 A 1/1958 Chase
3,799,172 A 3/1974 Szpur
(Continued)

FOREIGN PATENT DOCUMENTS

CN 102387759 A 3/2012
CN 103370016 A 10/2013
(Continued)

OTHER PUBLICATIONS

Buhl S., et al., "Humidity Influence on the Adhesion of Biomimetic Fibrillar Surfaces", International Journal of Materials Research, 2009, 100(8):1119-1126.
(Continued)

*Primary Examiner* — Kai H Weng
*Assistant Examiner* — Katherine-Ph Minh Pham
(74) *Attorney, Agent, or Firm* — Greenberg Traurig, LLP; Christopher C. Bolten; Albert K. Heng

(57) ABSTRACT

The present disclosure provides systems and devices for monitoring the pressure within a negative pressure system, such as a suction cannister. In one aspect, the system includes an anchor configured for positioning within an intestine of the patient at the anastomosis site and a source of negative pressure, such as a suction cannister, fluidly coupled to the anchor. A portable alarm device is coupled to the suction cannister and includes a trigger for detecting the pressure therein. A signal device emits a signal when this pressure is above a threshold level to ensure that the anchor remains securely in contact with the walls of the intestines at the anastomosis site. The alarm device includes a handle to allow a patient to grasp and carry the suction cannister, providing critical patient mobility during the recovery period.

21 Claims, 6 Drawing Sheets

(56) References Cited

U.S. PATENT DOCUMENTS 3,885,567 A 5/1975 Ross
4,627,837 A 12/1986 Gonzalo
4,716,900 A 1/1988 Ravo et al.
4,721,109 A 1/1988 Healey
5,358,496 A 10/1994 Ortiz et al.
5,425,739 A 6/1995 Jessen
5,534,007 A 7/1996 St. Germain et al.
5,558,642 A 9/1996 Schweich, Jr. et al.
5,594,038 A 1/1997 Kobayashi et al.
5,846,251 A 12/1998 Hart
5,876,448 A 3/1999 Thompson et al.
6,068,636 A 5/2000 Chen
6,103,255 A 8/2000 Levene et al.
6,146,416 A 11/2000 Andersen et al.
6,254,642 B1 7/2001 Taylor
6,325,798 B1 12/2001 Edwards et al.
6,379,379 B1 4/2002 Wang
6,398,758 B1 6/2002 Jacobsen et al.
6,514,282 B1 2/2003 Inoue
6,585,926 B1 7/2003 Mirzaee
6,733,519 B2 5/2004 Lashinski et al.
6,808,492 B2 10/2004 Snyder
6,926,724 B1 8/2005 Chu
7,025,791 B2 4/2006 Levine et al.
7,147,627 B2 12/2006 Kim et al.
7,267,694 B2 9/2007 Levine et al.
7,267,794 B2 9/2007 Amick
7,316,716 B2 1/2008 Egan
7,347,875 B2 3/2008 Levine et al.
7,509,175 B2 3/2009 Sparks et al.
7,547,312 B2 6/2009 Bauman et al.
7,631,153 B2 12/2009 Mahrla et al.
7,643,887 B2 1/2010 Imran
7,678,090 B2 * 3/2010 Risk, Jr. .................. A61M 1/92 604/289
7,744,914 B2 6/2010 Li et al.
7,766,973 B2 8/2010 Levine et al.
7,776,081 B2 8/2010 Zuidema et al.
7,815,591 B2 10/2010 Levine et al.
8,007,541 B2 8/2011 Benz et al.
8,083,758 B2 12/2011 Hsu et al.
8,114,045 B2 2/2012 Surti
8,118,774 B2 2/2012 Dann et al.
8,167,859 B2 5/2012 Shah et al.
8,182,527 B2 5/2012 Llanos et al.
8,187,254 B2 5/2012 Hissink et al.
8,211,186 B2 7/2012 Belhe et al.
8,221,783 B2 7/2012 Helmus et al.
8,282,598 B2 10/2012 Belhe et al.
8,323,229 B2 12/2012 Shin et al.
8,376,981 B2 2/2013 Laufer
8,398,669 B2 3/2013 Kim
8,435,283 B2 5/2013 Jordan et al.
8,491,612 B2 7/2013 Stopek et al.
8,597,224 B2 12/2013 Vargas
8,636,810 B2 1/2014 Rousseau
8,690,817 B2 4/2014 Assaf et al.
8,702,641 B2 4/2014 Belhe et al.
8,702,642 B2 4/2014 Belhe et al.
8,709,093 B2 4/2014 Robida et al.
8,753,407 B2 6/2014 Nguyen
8,801,647 B2 8/2014 Melanson et al.
8,821,429 B2 9/2014 Vargas
8,828,090 B2 9/2014 Terliuc
8,894,699 B2 11/2014 Kelley
8,900,268 B2 12/2014 Weidenhagen et al.
8,906,046 B2 12/2014 Anderson
8,926,593 B2 1/2015 Croizat et al.
9,044,300 B2 6/2015 Belhe et al.
9,173,734 B2 11/2015 Vargas
9,265,640 B2 2/2016 Harris et al.
9,339,272 B2 5/2016 Khosrovaninejad
9,398,982 B2 7/2016 Kleiner
9,402,630 B2 8/2016 Stopek et al.
9,439,790 B2 9/2016 Clerc et al.
9,511,208 B2 12/2016 Assaf et al.
9,517,122 B2 12/2016 Firstenberg et al.
9,526,640 B2 12/2016 Bertolino et al.
9,597,206 B2 3/2017 Seddon et al.
9,675,360 B2 6/2017 Baker
9,687,334 B2 6/2017 Williams et al.
9,750,596 B2 9/2017 Levine et al.
9,764,067 B2 9/2017 Fleury et al.
9,789,291 B2 10/2017 Assaf et al.
9,827,135 B2 11/2017 Fong et al.
9,980,727 B2 5/2018 Khosrovaninejad
10,058,413 B2 8/2018 Heiss
10,172,622 B2 1/2019 Kelley
10,271,972 B2 4/2019 Guler et al.
10,441,406 B2 10/2019 Firstenberg et al.
10,456,138 B2 10/2019 Khosrovaninejad
10,531,941 B2 1/2020 Hynes et al.
10,758,380 B2 9/2020 Bluecher et al.
10,779,928 B2 * 9/2020 Heiss ...................... A61M 1/66
10,835,248 B2 11/2020 Khosrovaninejad
10,973,675 B2 4/2021 Fong et al.
11,406,486 B2 8/2022 Heiss
11,534,149 B2 12/2022 Assaf et al.
11,589,869 B2 2/2023 Khosrovaninejad et al.
11,857,191 B2 1/2024 Khosrovaninejad
11,871,929 B2 1/2024 Khosrovaninejad et al.
11,903,865 B2 2/2024 Fong et al.
12,042,148 B2 7/2024 Khosrovaninejad
12,042,150 B2 7/2024 Khosrovaninejad et al.
12,048,433 B2 7/2024 Khosrovaninejad
12,059,368 B2 8/2024 Fong et al.
12,137,911 B1 11/2024 Khosrovaninejad
12,213,673 B2 2/2025 Augelli et al.
12,239,321 B2 3/2025 Augelli et al.
12,245,766 B2 3/2025 Augelli et al.
12,324,584 B2 6/2025 Khosrovaninejad
12,433,592 B2 10/2025 Khosrovaninejad et al.
12,447,262 B2 10/2025 Leveau-Mollier
12,478,377 B2 11/2025 Khosrovaninejad et al.
2001/0037808 A1 11/2001 Deem et al.
2002/0033226 A1 3/2002 Kohinata et al.
2004/0044358 A1 3/2004 Khosravi et al.
2004/0107004 A1 6/2004 Levine et al.
2004/0122527 A1 6/2004 Imran
2004/0147864 A1 7/2004 Lenker et al.
2005/0004663 A1 1/2005 Llanos et al.
2005/0033226 A1 2/2005 Kim
2005/0062610 A1 3/2005 Johnson
2005/0228409 A1 10/2005 Coppi
2005/0255230 A1 11/2005 Clerc et al.
2005/0256587 A1 11/2005 Egan
2005/0273075 A1 12/2005 Krulevitch et al.
2006/0064120 A1 3/2006 Levine et al.
2006/0095124 A1 5/2006 Benz et al.
2006/0112536 A1 6/2006 Herweck et al.
2006/0141012 A1 6/2006 Gingras
2006/0151568 A1 * 7/2006 Weller ............. A61B 17/07207 227/175.1
2007/0032879 A1 2/2007 Levine et al.
2007/0045229 A1 3/2007 Keenan et al.
2007/0179590 A1 8/2007 Lu et al.
2007/0262161 A1 11/2007 Davies
2007/0282247 A1 12/2007 Desai et al.
2007/0282452 A1 12/2007 Weitzner et al.
2008/0004566 A1 * 1/2008 Sloan .................. A61M 13/003 604/30
2008/0033244 A1 2/2008 Matsui et al.
2008/0039878 A1 2/2008 Williams et al.
2008/0161717 A1 7/2008 Gertner
2008/0167606 A1 7/2008 Dann et al.
2008/0195226 A1 8/2008 Williams et al.
2008/0208325 A1 8/2008 Helmus et al.
2008/0208357 A1 8/2008 Melanson et al.
2008/0249504 A1 10/2008 Lattouf et al.
2008/0255592 A1 10/2008 Hsu et al.
2009/0018606 A1 1/2009 Sparks et al.
2009/0069904 A1 3/2009 Picha
2009/0143722 A1 6/2009 Kim
2009/0143772 A1 6/2009 Kurtz

(56) References Cited

U.S. PATENT DOCUMENTS

| | | | |
|---|---|---|---|
| 2009/0220677 A1 | 9/2009 | Clerc et al. | |
| 2009/0276055 A1 | 11/2009 | Harris et al. | |
| 2010/0010519 A1 | 1/2010 | Stopek et al. | |
| 2010/0174381 A1 | 7/2010 | Benz et al. | |
| 2010/0179633 A1 | 7/2010 | Solem | |
| 2010/0282813 A1 | 11/2010 | Milliman | |
| 2011/0092950 A1 | 4/2011 | Shachar et al. | |
| 2011/0172760 A1 | 7/2011 | Anderson | |
| 2011/0202084 A1 | 8/2011 | Hoem et al. | |
| 2011/0295288 A1 | 12/2011 | Khosrovaninejad | |
| 2012/0095541 A1 | 4/2012 | Kramann | |
| 2012/0116528 A1 | 5/2012 | Nguyen | |
| 2013/0006382 A1 | 1/2013 | Behan | |
| 2013/0087597 A1* | 4/2013 | Shelton, IV | A61B 17/00 227/175.1 |
| 2013/0132054 A1 | 5/2013 | Sharma et al. | |
| 2013/0158463 A1 | 6/2013 | Assaf et al. | |
| 2013/0178879 A1 | 7/2013 | Laufer | |
| 2013/0218262 A1 | 8/2013 | Ishii et al. | |
| 2013/0231753 A1 | 9/2013 | Liddy et al. | |
| 2013/0274717 A1 | 10/2013 | Dunn | |
| 2013/0304101 A1 | 11/2013 | Stopek et al. | |
| 2014/0088622 A1 | 3/2014 | Rousseau | |
| 2014/0118029 A1 | 5/2014 | Tseng et al. | |
| 2014/0163664 A1 | 6/2014 | Goldsmith | |
| 2014/0222039 A1* | 8/2014 | Khosrovaninejad | A61B 17/08 606/151 |
| 2014/0350694 A1 | 11/2014 | Behan | |
| 2014/0371870 A1 | 12/2014 | Terliuc | |
| 2015/0045715 A1 | 2/2015 | Assaf et al. | |
| 2015/0119641 A1 | 4/2015 | Yamada | |
| 2015/0342760 A1 | 12/2015 | Christakis et al. | |
| 2016/0220256 A1 | 8/2016 | Khosrovaninejad | |
| 2016/0367352 A1 | 12/2016 | Heiss | |
| 2017/0027729 A1 | 2/2017 | Abu Dayyeh | |
| 2017/0071780 A1* | 3/2017 | Fong | A61F 5/449 |
| 2017/0087343 A1 | 3/2017 | Assaf et al. | |
| 2017/0189217 A1* | 7/2017 | Folan | A61F 5/0076 |
| 2017/0265849 A1 | 9/2017 | Assaf et al. | |
| 2017/0333042 A1 | 11/2017 | Sato | |
| 2018/0070800 A1 | 3/2018 | Yeung et al. | |
| 2018/0071078 A1 | 3/2018 | Majolagbe | |
| 2018/0235631 A1 | 8/2018 | Khosrovaninejad | |
| 2020/0000329 A1 | 1/2020 | Sugaya | |
| 2020/0338808 A1 | 10/2020 | Hulseman et al. | |
| 2021/0001019 A1* | 1/2021 | Elder | A61M 1/962 |
| 2021/0008336 A1* | 1/2021 | Rajagopalan | A61B 18/02 |
| 2021/0038224 A1 | 2/2021 | Khosrovaninejad | |
| 2021/0145624 A1 | 5/2021 | Fong et al. | |
| 2021/0205065 A1 | 7/2021 | Cote et al. | |
| 2021/0315578 A1 | 10/2021 | Khosrovaninejad et al. | |
| 2022/0000345 A1 | 1/2022 | Lalli et al. | |
| 2022/0105320 A1 | 4/2022 | Göbel | |
| 2022/0151465 A1 | 5/2022 | Johnsen et al. | |
| 2022/0250254 A1 | 8/2022 | Hulseman et al. | |
| 2022/0361880 A2 | 11/2022 | Khosrovaninejad et al. | |
| 2023/0083639 A1 | 3/2023 | Caplan et al. | |
| 2024/0058008 A1 | 2/2024 | Morris et al. | |
| 2024/0350295 A1 | 10/2024 | Fong et al. | |
| 2024/0407907 A1 | 12/2024 | Heiss | |
| 2025/0000683 A1 | 1/2025 | Fong et al. | |
| 2025/0041096 A1 | 2/2025 | Fong et al. | |
| 2025/0114232 A1 | 4/2025 | Fong et al. | |
| 2025/0275770 A1 | 9/2025 | Khosrovaninejad | |

FOREIGN PATENT DOCUMENTS

| | | | |
|---|---|---|---|
| CN | 103764069 | A | 4/2014 |
| CN | 204169953 | U | 2/2015 |
| CN | 108261577 | A | 7/2018 |
| EP | 1405612 | A1 | 4/2004 |
| EP | 2143389 | A1 | 1/2010 |
| EP | 2165665 | A1 | 3/2010 |
| EP | 2143388 | B1 | 6/2011 |
| EP | 1556097 | B1 | 8/2011 |
| EP | 1746941 | B1 | 11/2011 |
| EP | 2395942 | A1 | 12/2011 |
| EP | 2347723 | B1 | 12/2012 |
| EP | 2286739 | B1 | 1/2013 |
| EP | 2604195 | A1 | 6/2013 |
| EP | 1492585 | B1 | 6/2016 |
| EP | 2143387 | B1 | 12/2016 |
| EP | 1647231 | B1 | 11/2017 |
| FR | 2846868 | A1 | 5/2004 |
| FR | 2941858 | A1 | 8/2010 |
| JP | 2000316979 | A | 11/2000 |
| JP | 2005519709 | A | 7/2005 |
| JP | 2005524485 | A | 8/2005 |
| JP | 2007069003 | A | 3/2007 |
| JP | 2007513685 | A | 5/2007 |
| JP | 2010502289 | A | 1/2010 |
| JP | 2012050841 | A | 3/2012 |
| JP | 2012517255 | A | 8/2012 |
| JP | 2014527854 | A | 10/2014 |
| WO | WO-03094785 | A1 | 11/2003 |
| WO | WO-2007045229 | A1 | 4/2007 |
| WO | WO-2008030403 | A1 | 3/2008 |
| WO | WO-2008039223 | A1 | 4/2008 |
| WO | WO-2010002291 | A1 | 1/2010 |
| WO | WO-2010009291 | A1 | 1/2010 |
| WO | WO-2010018571 | A2 | 2/2010 |
| WO | WO-2010092291 | A1 | 8/2010 |
| WO | WO-2011085234 | A1 | 7/2011 |
| WO | WO-2011120047 | A1 | 9/2011 |
| WO | WO-2013014353 | A1 | 1/2013 |
| WO | WO-2013014355 | A1 | 1/2013 |
| WO | WO-2013026474 | A1 | 2/2013 |
| WO | WO-2014193949 | A2 | 12/2014 |
| WO | WO-2017048989 | A1 | 3/2017 |
| WO | WO-2017191500 | A1 | 11/2017 |
| WO | WO-2017201504 | A1 | 11/2017 |
| WO | WO-2018089773 | A1 | 5/2018 |
| WO | WO-2019077218 | A1 | 4/2019 |
| WO | WO-2020152640 | A1 | 7/2020 |
| WO | WO-2024170414 | A1 | 8/2024 |
| WO | WO-2024194771 | A2 | 9/2024 |

OTHER PUBLICATIONS

Extended European Search Report for European Application No. 22170158.4, mailed Oct. 11, 2022, 8 pages.

International Search Report and Written Opinion dated Aug. 19, 2022 in Int'l PCT Patent Application Serial No. PCT/US2022/026558, 10 pages (0510).

International Search Report and Written Opinion dated Mar. 20, 2019 in Int'l PCT Appl. Serial No. PCT/FR2018/052388, 06 pages (0310).

International Search Report and Written Opinion dated May 7, 2010 in Int'l PCT Patent Application Serial No. PCT/FR2010/050210, 6 pages (0110).

International Search Report and Written Opinion dated Sep. 4, 2012 in Int'l PCT Patent Appl. Serial No. PCT/FR2012/051576, 7 pages (0210).

International Search Report and Written Opinion from corresponding PCT Application No. PCT/FR2020/050889, Sep. 10, 2020, 6 pages (0410).

Moon CM., et al., "Comparison of a Newly Designed Double-Layered Combination Covered Stent and D-Weave Uncovered Stent for Decompression of Obstructive Colorectal Cancer: A Prospective Multicenter Study", Dis Colon Rectum, 2010, vol. 53, pp. 1190-1196.

Shim CS., et al., "Through-the-Scope Double Colonic Stenting in the Management of Inoperable Proximal Malignant Colonic Obstruction: a Pilot Study", Endospcopy, 36(05):426-431 (May 2004).

Shomura Y., et al., "Composite Material Stent Comprising Metallic Wire and Polylactic Acid Fibers, and Its Mechanical Strength and Retrievability", Acta Radiol., May 2009, vol. 50, No. 4, pp. 355-359.

Mukai, et al., The economic burdens of anastomotic leakage for patients undergoing colorectal surgery in Japan, Asian Journal of Surgery, 46:4323-4329 (2023).

(56) References Cited

OTHER PUBLICATIONS

Invitation to Pay Additional Fees and Partial Search Report dated Jun. 28, 2024 in Int'l PCT Patent Appl. Serial No. PCT/IB2024/052550 (061001).

International Search Report and Written Opinion dated Oct. 2, 2024 in Int'l PCT Patent Appl. Serial No. PCT/IB2024/052550 (061001).

Heiss, et al., Treatment of anastomotic leak in colorectal surgery by endoluminal vacuum therapy with the VACStent avoiding a stoma—a pilot study, Langenbeck's Archives of Surgery, 409:234, pp. 1-12 (Jul. 2024).

Lange, et al., Clinical implantation of 92 VACStents in the upper gastrointestinal track of 50 patients-applicability and safety analysis of an innovative endoscopic concept, Front. Surg. 10:1182094, doi:10.3389/fsurg.2023.1182094 (May 2023).

Lange, et al., VACStent: Combining the benefits of endoscopic vacuum therapy and covered stents for upper gastrointestinal tract leakage, Endosc. Int. Open, 09:E971-E976 (May 2021).

* cited by examiner

SYSTEMS AND DEVICES FOR MONITORING NEGATIVE PRESSURE DEVICES

CROSS REFERENCE TO RELATED APPLICATIONS

This application claims priority to U.S. Provisional Application No. 63/184,360, filed May 5, 2021, entitled Systems and Devices for Monitoring Negative Pressure Devices, the contents of which are incorporated herein by reference in entirety.

FIELD

The present disclosure generally relates to systems and devices for monitoring negative pressure devices for use with patients and more particularly to portable alarm devices for continuously monitoring the pressure of an internal bypass device to protect against leakage in an anastomosis site following a bowel resection procedure.

BACKGROUND

In some instances, a segment of a patient's bowels must be removed to treat certain blockages and diseases, such as colorectal cancer, diverticulitis, severe bleeding, obstructions, and the like. In these bowel resection procedures, a physician dissects and removes a diseased or obstructed portion of the large intestine and then reconnects the healthy ends of the intestine with tiny staples or sutures, often referred to as a bowel anastomosis. The most serious complication occurring with bowel resection procedures is anastomotic leakage, which can occur when the healing process is delayed or incomplete. Anastomotic leakage allows feces and other waste matter to leak into the abdominal cavity, which can lead to a dangerous infection or sepsis. To prevent this from occurring, the anastomosis site must be protected immediately after surgery.

Traditionally, to prevent anastomotic leakage, surgeons create an external bypass of the anastomosis site, referred to as a diverting ostomy. In this procedure, the surgeon creates a temporary opening or stoma, (e.g., an artificial anus) to divert the intestines to this opening. The surgeon then attaches an ostomy bag to the opening in the abdomen to collect the patient's feces and other waste matter during the healing period. Unfortunately, ostomies are debilitating for patients, prone to complications and costly and inefficient in terms of patient management. In addition, ostomies require a second surgery to reverse.

To overcome the limitations of diverting ostomy procedures, internal temporary bypass devices have been created. These bypass devices typically include a flexible sheath that is introduced into the colon and placed against the internal walls of the colon at the anastomosis site. The bypass device eliminates any contact between the tissue and feces or other waste matter traveling through the intestines, thereby ensuring the cleanliness of the anastomosis. After healing is complete, the sheath can be removed from the patient through a routine endoscopic procedure without requiring a second surgery.

One of the challenges with internal bypass devices is ensuring that they remain in secure contact with the bowel tissue around the anastomosis to prevent migration of the sheath or any leakage of bowel contents around the sheath and into the patient's abdomen. To overcome this challenge, bypass devices may include a negative suction or vacuum pressure system that provides a continuous negative pressure to the external walls of the sheath such that the sheath remains in close contact with the internal walls of the bowl around the anastomosis site. This negative suction pressure is typically supplied to the peripheral walls of the sheath with one or more fluid lines or catheters. The fluid lines are coupled to an external source of negative pressure, such as a suction cannister or the like.

While these new bypass devices have been extremely effective, they suffer from certain drawbacks. For example, continuous suction pressure must be applied to the bypass sheath throughout the entire healing period. If any part of the pressure system suffers a loss in negative pressure, the outer walls of the sheath may lose contact with the intestines and allow migration of the sheath and/or leakage of feces or waste matter through the anastomosis. Accordingly, the pressure of the suction system must be constantly monitored. In the event of a loss of negative pressure, a health care practitioner must be immediately alerted so that the system can be replaced before the sheath ceases to function as intended.

Another drawback with existing negative pressure systems designed for use with internal bypass devices is that the suction canisters are typically supplied with negative pressure by a separate vacuum device. Therefore, to provide patient mobility during the healing period in the hospital, the storage canisters must either be disconnected from the vacuum device altogether or the patient must move around with the entire system. This not only subjects the patient to traveling with more devices but also with extra tubing, which must be clipped and secured to prevent falls. These troublesome systems are inconvenient to the patient, or to the therapists who assist them in movement.

To further enhance patient mobility, suction canisters have been designed that can be previously supplied with negative pressure prior to use by the patient. Since these suction cannisters already have a negative or vacuum pressure, they do not require attachment to a separate tube for connection to the vacuum source. Although this provides some improvement in patient mobility, a suction cannister alone is typically difficult for the patient to easily grip and carry.

What is needed, therefore, are improved systems and devices for protecting an anastomosis site after bowl resection surgery. It would be particularly desirable to provide devices that produce a clear alert signal to the health care professional when there is loss in pressure in the negative pressure system that secures the internal bypass sheath to the anastomosis site. It would be further desirable to provide suction devices that are portable to allow the patient to be mobile during the recovery period to enhance GI motility and improve the patient's overall quality of life during this period.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides systems and devices for monitoring negative pressure devices for use with patients. In some aspects, the systems create an internal bypass within a target area of the GI tract of a patient to allow feces and other waste matter to pass through the target area without contacting the walls of the GI tract at the target area. The target area may be, for example, an anastomosis site created after bowel resection surgery to treat certain blockages and diseases, such as colorectal cancer, diverticulitis, severe bleeding, obstructions, and the like.

In one aspect of the present disclosure, an internal bypass system for an anastomosis site in a GI tract of a patient comprises an anchor configured for positioning within an intestine of the patient at the anastomosis site and a source of negative pressure, such as a suction cannister, fluidly coupled to the anchor. The system further includes an alarm device having a trigger for detecting a pressure in the suction cannister and a signal device configured to emit a signal based on the pressure to ensure that the anchor remains securely in contact with the walls of the intestines at the anastomosis site.

The systems and devices of the present disclosure respond to the pressure from within the negative pressure system to produce a clear alert signal if any part of the pressure system suffers a loss in suction pressure. This allows a healthcare practitioner to, for example, either diagnose the issue with the negative pressure system or replace one or more components of the system to ensure that the anchor remains in place throughout the healing period, thereby preventing the leakage of feces or waste matter through the anastomosis.

In certain embodiments, the anchor comprises a flexible sheath having outer walls and an internal channel for allowing passage of matter through the sheath. The anchor may further comprise a stent coupled to the sheath and configured to provide an outward radial force to the sheath. The negative pressure system comprises one or more tubes fluidly coupled to an outer wall of the sheath and at least one suction canister fluidly coupled to the tubes. The suction canister may be coupled to a source of negative or vacuum pressure, or the cannister itself may be the source of negative pressure. The combination of the stent and the negative pressure system secures the flexible sheath against the colonic wall to prevent migration of the sheath and/or leakage around the sheath.

The alarm device preferably comprises a main body configured for removable attachment to the suction cannister. The main body is configured to allow a patient to grasp the device and carry the suction cannister, thereby providing critical patient mobility during the recovery period.

In certain embodiments, the main body of the portable alarm device comprises a coupling device for removably attaching the main body to the suction cannister. In some exemplary embodiments, the coupling device comprises a fastener sized to pass through an opening of the suction cannister and an opening of the main body. In some non-limiting aspects, the opening of the suction cannister is a hole located on a projection of the suction cannister, such as a tab or the like.

In certain embodiments, the trigger may include a movable element disposed in contact with a surface of the suction cannister and configured to move from a first position to a second position when the pressure within the suction cannister reaches the threshold level. In these embodiments, the system further comprises a tactile sensor positioned such that the movable element contacts the tactile sensor when the pressure reaches the threshold level. In an exemplary embodiment, the tactile sensor is coupled to the signal device and configured to activate the signal device when the expandable element contacts the tactile sensor.

In a preferred embodiment, the movable element is an expandable element that expands in response to the pressure reaching the threshold level. The main body and the suction cannister are positioned by the coupling device such that the surface of the tactile sensor is contactable by the surface of the expandable element in its expanded configuration. In this embodiment, the coupling device serves multiples purposes: to secure the alarm device to the suction cannister for portability and to position the tactile sensor such that the expandable element contacts the tactile sensor upon expansion. Thus, the unique and simple design of the coupling device not only allows for reproducible connection, but is also lightweight and does not burden the patient. Another advantage of the coupling device of some embodiments of the present disclosure, is that it is configured for connecting the main body to suction cannisters that are already widely used in the medical setting, such as the Jet-Vac canister produced by PFM Medical, Inc.

In certain embodiments, the main body comprises an elongate body having opposing ends configured for removable attachment to first and second suction cannisters. In these embodiments the device comprises first and second sensors. The first sensor is configured to detect pressure within the first suction cannister and the second sensor is configured to detect pressure within the second suction cannister.

In an exemplary embodiment, the elongate body comprises a handle which enables the patient to easily carry both suction cannisters. In some embodiments, the elongate body is rigid and has a length in the range of about 6 to 18 inches. This provides sufficient space for a handgrip by a patient and for connecting two separate suction cannisters to the alarm device.

In certain embodiments, the signal device comprises a power supply and suitable electronics coupled to the tactile sensor to produce an alarm or alert signal indicating that the internal pressure of the suction cannister is above the threshold level. In other embodiments, the power supply and electronics may be separate from the alarm device and coupled to the tactile sensor through a wireless connection, such as Bluetooth or the like. The alarm or alert signal may be any signal that alerts the patient and/or the health care professional that the container(s) are full and must be replaced. For example, the signal may comprise an audible alert, a visual alert or it may be transmitted by direct connection or wirelessly to a remote location, such as the nurse station or other suitable location.

In another aspect of the invention, a portable alarm device is provided for use with an internal bypass system for an anastomosis site. The alarm device comprises a main body configured for removable attachment to a suction cannister and at least one sensor coupled to the main body and configured to detect a pressure from an interior of the suction cannister. The alarm device further includes a signal device coupled to the sensor and configured to emit a signal when pressure within the suction cannister is above a threshold level. One of the advantages of this alarm device is that main body comprises a elongate portion that functions as a handle to allow a patient to grasp the device and carry the suction cannister, thereby providing patient mobility during the recovery period.

In certain embodiments, the main body of the portable alarm device comprises a coupling device for removably attaching the main body to the suction cannister. In some exemplary embodiments, the coupling device comprises a fastener sized to pass through an opening of the suction cannister and an opening of the main body. In some non-limiting aspects, the opening of the suction cannister is a hole located on a projection of the suction cannister, such as a tab or the like.

In certain embodiments, the system may include an expandable element disposed in contact with a surface of the suction cannister and configured to expand when the pressure within the suction cannister reaches the threshold level. In these embodiments, the sensor comprises a tactile sensor positioned such that the expandable element contacts the tactile sensor when the pressure reaches the threshold level. In an exemplary embodiment, the tactile sensor is coupled to the signal device and configured to activate the signal device when the expandable element contacts the tactile sensor.

In a preferred embodiment, the main body and the suction cannister are positioned by the coupling device such that the surface of the tactile sensor is contactable by the surface of the expandable element of the suction cannister in its expanded configuration. In this embodiment, the coupling device serves multiples purposes: to secure the alarm device to the suction cannister for portability and to position the tactile sensor such that the expandable element contacts the tactile sensor upon expansion.

In another aspect of the invention, a portable alarm device is provided for use with an internal bypass system for an anastomosis site. The alarm device comprises an elongate body with first and second opposing ends. Each opposing end is configured for removable attachment to first and second suction cannisters. The device further comprises a first trigger configured to detect a pressure from an interior of the first suction cannister and a second trigger configured to detect a pressure from an interior of the second suction cannister. The device further comprises a signal device coupled to each trigger and configured to emit a signal when the pressure within the first or second suction cannister is above a threshold level.

According to an exemplary embodiment, the elongate body comprises a handle that can be easily grasped and carried by the patient. In some embodiments, the elongate body of the device is rigid and has a length in the range of about 6 to 18 inches. An elongate body having a length in this range would allow the device to connect to two canisters at once, one at each end.

In some embodiments, the alarm device comprises first and second coupling devices for removably attaching the elongate body to the first and second suction cannisters. In an illustrative embodiment, each of the first and second coupling devices comprises a fastener sized to pass through an opening of each of the first and second suction cannisters and an opening of the main body. This unique design of a three-part portable system lends itself to improving patient mobility during the recovery period.

In certain embodiments, the first and second triggers each comprise an element having a contact surface configured to contact a surface of an expandable element of one of the first and second suction cannisters, the expandable element being configured to expand when the pressure within one of the first and second suction cannisters reaches the threshold level. In other embodiments, the device further comprises first and second tactile sensors positioned such that the expandable element of one of the first and second suction cannisters contacts the element of one of the first and second tactile sensors when the pressure reaches the threshold level.

In an exemplary embodiment, the first and second tactile sensors are coupled to the signal device and configured to activate the signal device when an expandable element of either one or both of the first and second suction cannisters contacts one of the tactile sensors. The elongate body of the portable device and the first and second suction cannisters may be positioned by the first and second coupling devices such that the surface of the element of one of the first and second tactile sensors is contactable by the surface of the expandable element of one of the first and second suction cannisters in its expanded configuration.

In exemplary embodiments, the signal device comprises a power supply. In certain embodiments, the signal comprises an audible alert. In other embodiments, the signal comprises a visual alert. In yet other exemplary embodiments, the signal comprises an audible alert. In some embodiments, the signal comprises data and the device further comprises a transmitter for transmitting the data to a remote location. It is understood that the signal may also be a combination of any of these types of alerts.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DETAILED DESCRIPTION OF THE PREFERRED EMBODIMENTS

Particular embodiments of the present disclosure are described hereinbelow with reference to the accompanying drawings; however, it is to be understood that the disclosed embodiments are merely exemplary of the disclosure and that the disclosure may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail. It should be understood also that the drawings are not drawn to scale and are not intended to represent absolute dimensions or relative size. Instead, the drawings help to illustrate the concepts described herein.

The present disclosure provides systems and devices for creating an internal bypass within a target area of the GI tract of a patient to allow feces and other waste matter to pass through the target area without contacting the walls of the GI tract at the target area. The target area may be, for example, an anastomosis site in the colon, rectum or anal passage created after bowel resection surgery to treat certain blockages and diseases, such as colorectal cancer, diverticulitis, severe bleeding, obstructions and the like. The bypass device may be secured to the anastomosis site with a negative pressure system, such as one or more suction cannisters coupled to the bypass device via suitable medical tubing, or the like. The present disclosure further provides a portable alarm device that responds to the pressure from within the suction cannister(s) and produces an alert signal to the health care professional when the pressure reaches a threshold level that would no longer be sufficient to secure the bypass device to the anastomosis site.

The portable alarm device is coupled to one or more suction cannisters and provides a handle for grasping and holding the cannister(s). This design allows the storage canisters to be portable to allow the patient to walk within their recovery room or about the halls of the hospital, as their normal mobility is restored, without disrupting the continuous application of negative or vacuum pressure to the bypass device.

Figure 1:
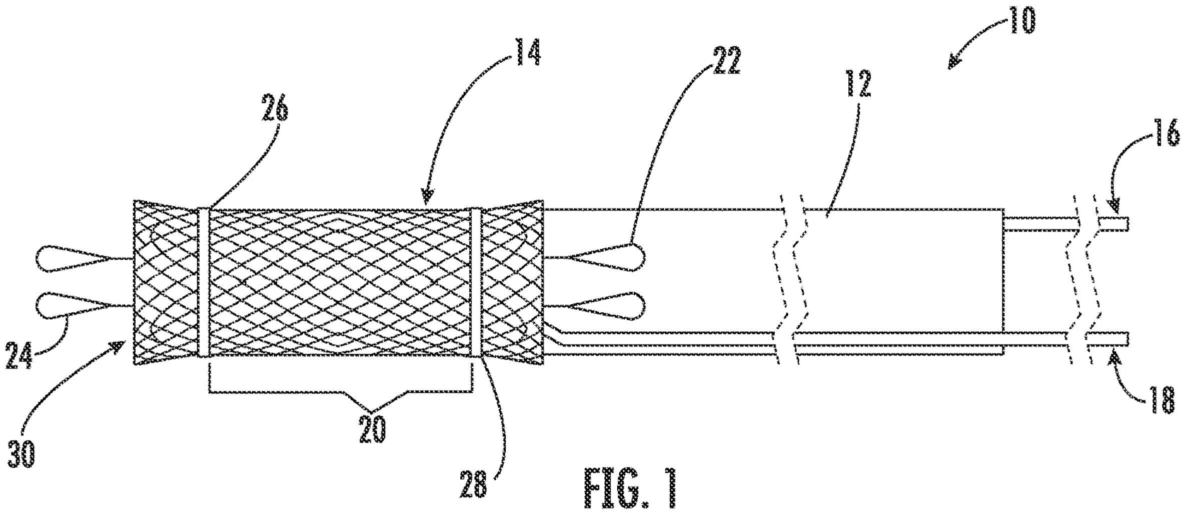
FIG. 1 is a side view of an anchor for an internal bypass system according to the present disclosure.
Figure 7:
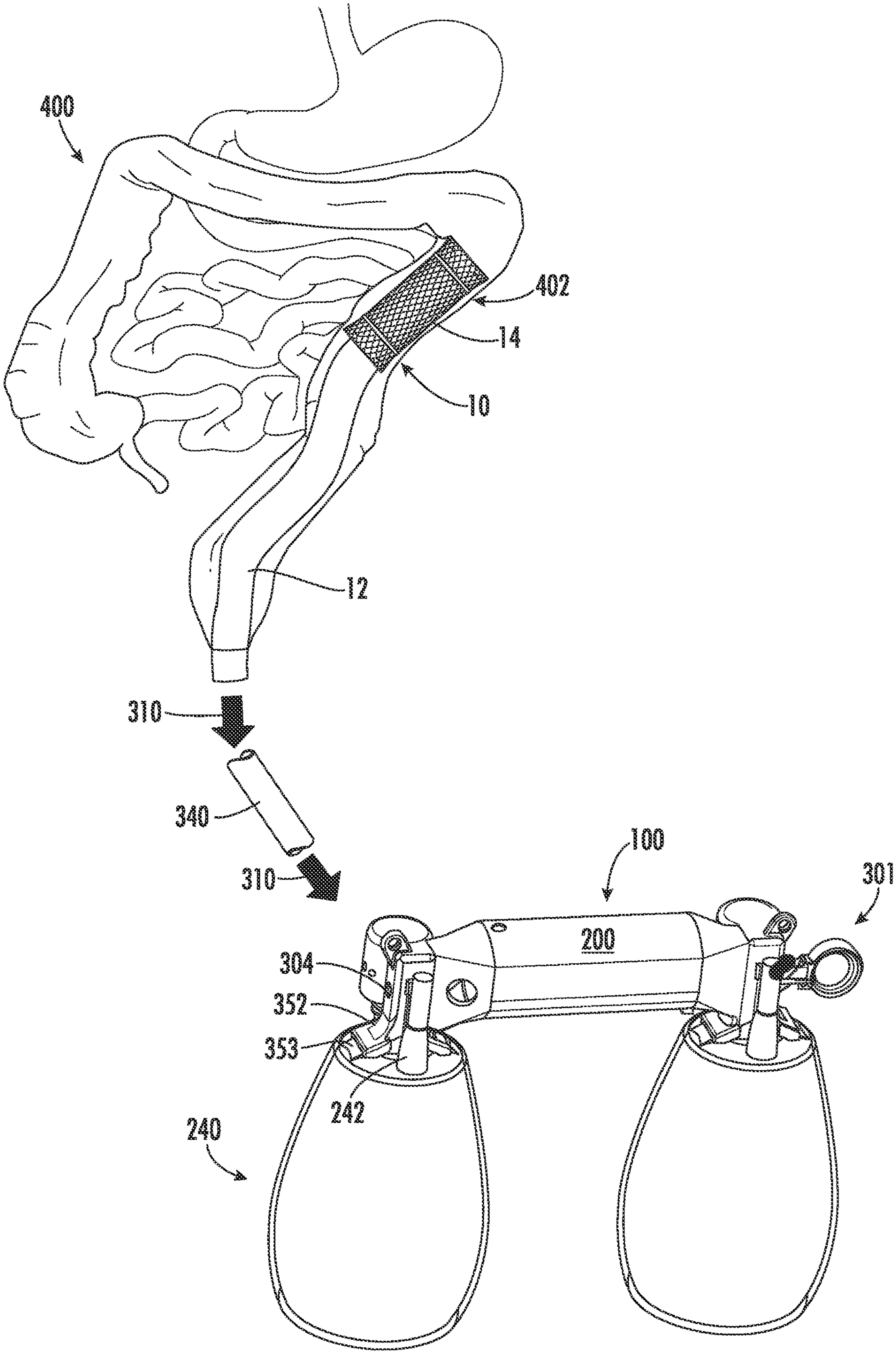
FIG. 7 illustrates the internal bypass device of the present invention in use at an anastomosis site within the GI tract of a patient.

Referring now to FIG. 1, an anchor 10 for providing an internal bypass at a target site within the GI tract of the patient will now be described. As shown, anchor 10 comprises an elongate flexible sheath 12 having outer walls and an internal channel for allowing passage of feces and other waste matter therethrough. Sheath 12 has a length selected to extend from the target site in the GI tract through the patient's intestines and anus to a location external to the patient (see FIG. 7). Sheath 12 includes a proximal end coupled to a collection vessel (not shown) that is located within, or external to, the patient's body. Sheath 12 may comprise a biocompatible elastomer material, such as silicone or polyurethane.

Anchor 10 further comprises a stent 14 coupled to sheath 12 and configured to provide an outward radial force against sheath 12 or against the walls of the intestines. Stent 14, in combination with the negative pressure system described below, functions to hold open the target area within the GI tract such that feces and other waste matter will pass through sheath without contacting the walls around the anastomosis site. A more complete description of a suitable sheath and stent for use in bypass device 10 can be found in U.S. Pat. No. 9,339,272, the complete disclosure of which is incorporated herein by reference for all purposes.

Bypass device 10 further comprises one or more suction tubes 16, 18 extending along the outer periphery of sheath 12. Suction tubes 16, 18 have proximal ends that are coupled to a negative or vacuum pressure system for providing a negative pressure around the walls of sheath 12 and/or stent 14. This negative pressure functions to suction the outer walls of sheath 12 and stent 14 within a vacuum chamber area 20 to the inner walls of the intestines. In certain embodiments, bypass device may further include a distal covering ring 30 and one or more sealing rings 26, 28 extending around stent 14 to securely fasten stent 14 to the distal end of sheath 12. In addition, device 10 may include distal and/or proximal retrieval loops 22, 24 for facilitating removal of the device 10 after the anastomosis has fully healed.

Figure 2:
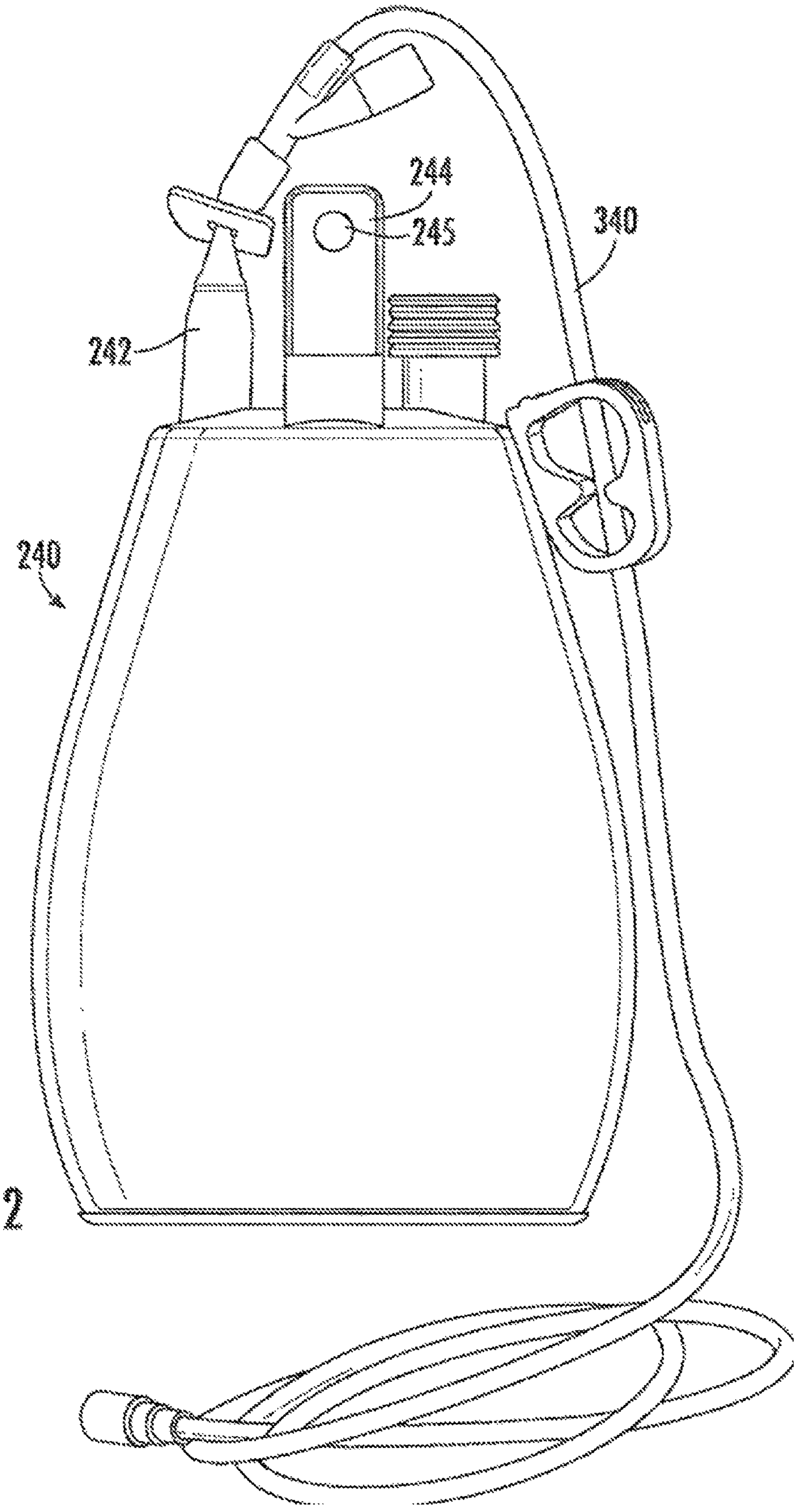
FIG. 2 is a perspective view of an exemplary suction cannister for use with an internal bypass system according to the present disclosure.

As shown in FIG. 2, the negative pressure system of the present disclosure further comprises one or more suction cannister(s) 240 coupled to suction tubes 16, 18 in FIG. 1 via medical tubing 340. Suction cannister 240 provides a source of negative or vacuum pressure to suction tubes 16, 18. In some embodiments, suction cannister 240 is a standard suction cannister made of a lightweight plastic, such as those provided by PFM Medical, Inc. In other embodiments, suction cannister 240 may be another fluid management system known in the medical art. For example, the container may be the Medi-Vac suction canister sold by Cardinal Health, Inc., which is also a rigid plastic container but has a different structure than that of the Jet-Vac canister. In yet other embodiments, suction cannister 240 is a custom-designed one for use with the portable device of this disclosure.

Suction cannister 240 further comprises a projection 244 with an opening 245 on its top surface. In some embodiments discussed below, the main body of the portable device or accessory components to the portable device may comprise an insert, such as a fastener, which is sized to pass through opening 245. In the embodiment depicted in FIG. 2, the projection 244 of the suction canister is a plastic tab that includes opening 245. It is understood that suction cannister 240 may comprise a different structure altogether than what is shown in FIG. 2. For example, suction cannister 240 may not have projection 244 and the coupling to the portable alarm device 100 may be accomplished by a different mechanism than that of the fastener described below.

The representative suction cannister 240 further comprises an inflow adaptor 242. Inflow adaptor 242 is capable of further attachment to medical tubing 340. In other embodiments of suction cannister 240, inflow adaptor 242 may be located elsewhere on the container instead of its top surface. For example, the location of inflow adaptor 242 may actually be somewhere near the bottom of the suction cannister. In some embodiments, it may be useful for the inflow adaptor 242 to comprise a control valve to allow for starting or stopping flow.

FIG. **3*a* is a perspective view of a portable alarm device 100 according to the present invention. As shown, alarm device 100 comprises a main body 200 removably coupled to two suction cannisters 240. Main body 200 comprises an elongated portion 210, suitable for accommodating a handgrip of the average-sized patient's hands, and two opposing ends 350. Main body 200 or its elongated portion 210 may be about 6-10 inches in length to accommodate the coupling of two canisters, such as two 600 mL Jet-Vac canisters. Alternatively, main body 200 or elongated portion 210 may be longer than 10 inches to couple to wider-diameter canisters, or to accommodate a larger-size handgrip. In a preferred embodiment, the total length of main body 200 or elongated portion 210 is no more than 18 inches so that device 100 is lightweight and manageable to move. While these are descriptions of the preferred lengths of main body 200 or elongated portion 210, it should be understood that device 100** may be shorter or longer than the lengths described herein.

Elongated portion 210 has a generally angular shape, like a rectangular block. The perpendicular cross-section of elongate portion 210, therefore, may be irregularly shaped and include sharp angles. In other embodiments, elongate portion 210 of main body 200 has a generally tubular or curvilinear shape, such as with a curved surface, similar to a standard bicycle handlebar. In these instances, the cross section of elongate portion 210 is generally circular or oval in nature. Main body 200 may alternatively be a combination of these shapes, with angular edges at opposing ends 350 of the device and tubular in the middle portion where the hand surrounds it. Main body 200 may be substantially rigid to be suitable for a robust grip. However, it may be at least partially covered with rigid or non-rigid padding to increase comfort while a patient holds it. The main body 200 may alternatively be covered at least in part by a material having roughness suitable for a non-slip hand grip. The covering could instead be a disposable liner. No matter the material, the surface of the device or the covering should be such that can be disposed of or easily disinfected with standard cleaning supplies used for cleaning medical equipment known in the art.

Elongate portion 210 of device 100 serves as a handle while opposing ends 350 include the coupling assemblies. In this embodiment, since opposing ends 350 are not constituents of the handle portion of the device, they may have a different shape altogether. For example, opposing ends 350 may include the coupling device and sensors and thus, may be modularly designed and irregularly shaped.

Figure 3A:
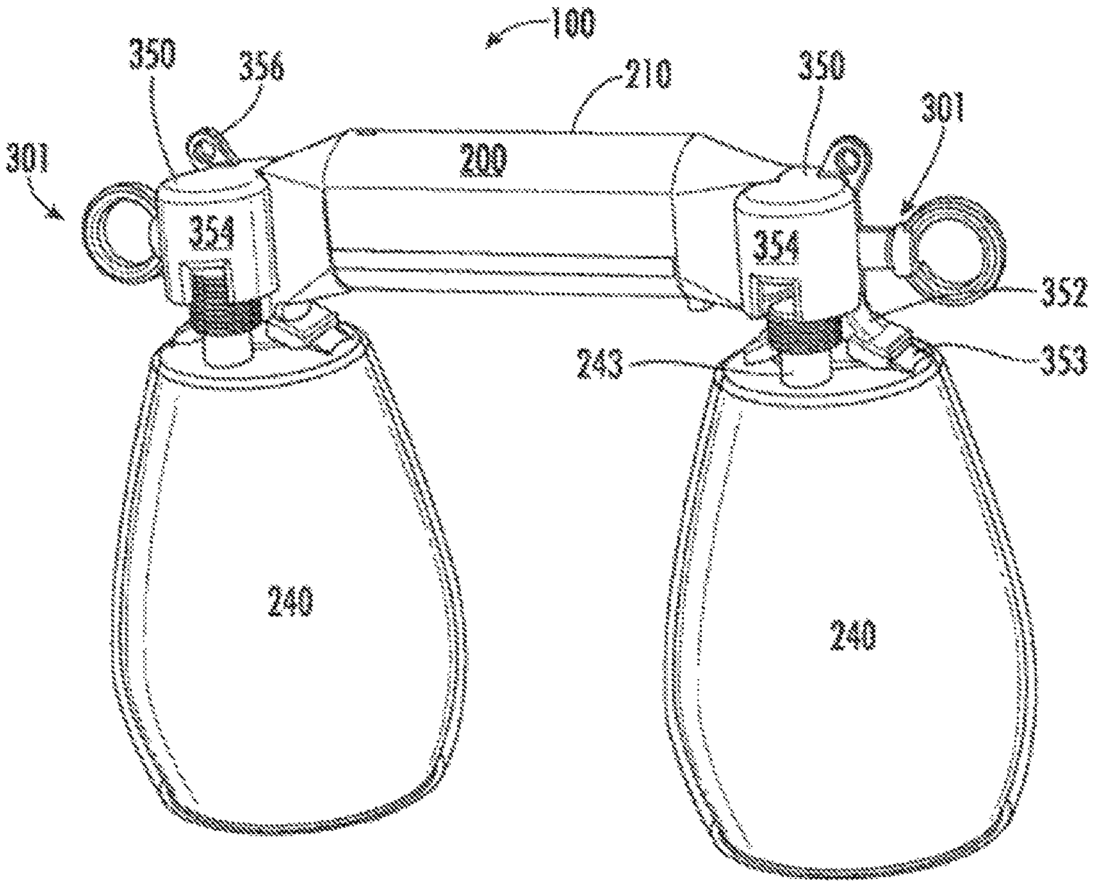
FIG. 3A is a perspective view of a portable alarm device of the present disclosure coupled to two representative suction cannisters.

One embodiment of opposing ends 350 is shown in FIG. 3*a*. In this embodiment, each opposing end 350 comprises a hollow partial enclosure 354 for receiving and partially enclosing an expandable element 243 of suction cannister 240, which is discussed in further detail below. Opposing ends 350 further include an opening 304 shown more clearly in FIG. 7. Opening 304 is sized for removable insertion of a fastener, such as a pin 303, shown in FIG. 4. In the exemplary embodiment shown in FIG. 3*a*, each opposing end 350 further includes a hanging tab 356 configured to allow the patient or clinician the option of hanging the device, whether alone or while coupled to suction cannisters 240. This would be useful in the instances when the patient's hands are occupied as they move about. For example, in the earlier stages of their recovery, the patient may be asked by a physical therapist to walk while holding onto a walker with both hands. In another example, the patient may find it more convenient to hang the device bedside to keep surfaces in their immediate vicinity clear for other uses.

Opposing end 350 may further include a base 352 that engages with the surface of suction cannister 240 and at least partially houses projection 244 of suction cannister 240. In some embodiments, as shown in FIG. 3*a* and more clearly in FIG. 7, base 352 includes a partially hollow enclosure with protruding feet 353 that make contact with top surface of suction cannister 240. For example, projection 244 may be inserted into the hollow space within base 352 so that its opening 245 would align with corresponding opening 304. In this manner, base 352 and projection 244 become locked in position when pin 303 is removably inserted through both openings. It should be understood that there may be multiple different embodiments of the surface of suction cannister 240 and coupling device 301, and therefore the design of the device, including its opposing ends 350, will be contingent on the structure necessary to achieve a secure connection between the device and container.

In some embodiments, suction cannister 240 comprises an expandable element 243 on a surface of cannister 240. Expandable element 243 may be in a contracted configuration as exemplified in the image of the right suction cannister 240 of FIG. 3*a*, or in an expanded configuration as shown on the left suction cannister 240 in FIG. 3*a*. In other embodiments, expandable element 243 may be an integral piece of suction cannister 240. In other embodiments, expandable element 243 is a separate component suitably coupled to suction cannister 240. Expandable element 243 may be a component of portable alarm device 100. In these embodiments, other components of suction cannister 240 transduce a signal of the pressure reaching a threshold level to expandable element 243, forcing it to expand. Regardless of its location, expandable element 243 is configured to expand in response to the pressure within suction cannister 240.

In an exemplary embodiment, expandable element 243 is configured to expand when the pressure within the suction cannister 240 reaches a threshold level. For example, if there is a loss of negative or suction pressure, the threshold pressure is reached, which causes expandable element 243 to move into the expanded configuration. In an exemplary embodiment, when expandable element 243 expands into its expanded configuration, its surface makes contact with the surface of a sensor element 307 of a tactile sensor 306 of device 100, as shown in the exploded portion of FIG. 3*b*.

The threshold pressure level that will trigger expandable element 243 may vary depending on the suction cannister used with the system. At a minimum, this threshold level will comprise a pressure that is high enough such that the internal bypass device is no longer capable of holding open the target area within the GI tract such that feces and other waste matter will pass through sheath without contacting the walls around the anastomosis site. In certain embodiments, the threshold pressure level will be based on an actual pressure value. A vacuum or suction pressure can generally be created with a pressure level below atmospheric pressure, or below about 760 mm Hg, which will vary based on the altitude of the suction canister, the temperature and other factors. In order to provide sufficient suction pressure to the internal bypass device, the pressure within the suction cannister is preferably at a level well below atmospheric pressure, e.g., about 480 mm Hg, or less. In certain embodiments, the threshold pressure level is a pressure greater than about 400 mm Hg, preferably greater than about 480 mm Hg.

In other embodiments, the threshold pressure level will be based on a percentage of the pressure level set by the individual suction canister. For example, certain commercial cannisters are set such that the trigger will expand when the pressure within the cannister is about 80% of the predetermined vacuum pressure within the system. In other cases, the pressure level may be set at other percentages, such as 90%, 75%, 50%, etc., depending on the capabilities of the individual suction cannister.

It will be recognized by those skilled in the art that expandable element 243 may have a different structure than described above. For example, element 243 may be rectangular, circular, square, conical, or domed-shaped. In addition, element 243 may be designed to move from one position to another, or to simply translate or extend in one direction, when the threshold pressure has been reached in cannister 240 (rather than expanding).

Figure 3B:
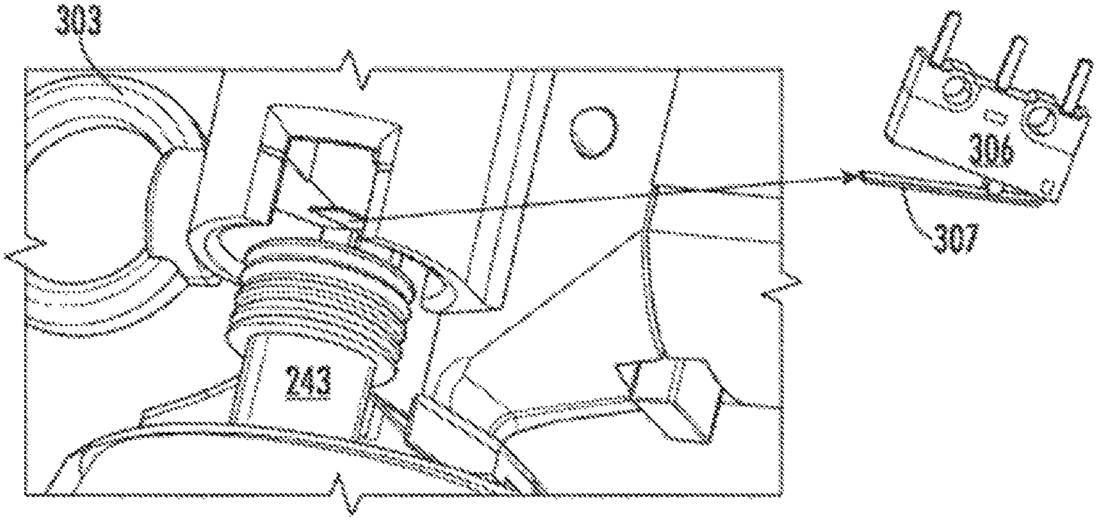
FIG. 3B is an exploded view of a portion of the portable alarm device of FIG. 3A.

In certain embodiments, sensor 306 is a type of pressure sensor, such as a tactile pressure sensor. In some embodiments, a surface of the tactile pressure sensor is configured to be contacted by the surface of expandable element 243 of FIG. 3*b*. In certain embodiments, the tactile sensor is further coupled to signal device 227. In one aspect, as shown in FIG. 3*b*, element 307 of sensor 306 has a surface which is acted upon by the expansion of the expandable element 243. It should be understood that there are many different types of switches, including snap-action switches, such as sensor 306 of FIG. 2*b*, which may be used to detect the force of expansion of expandable element 243.

Figure 4:
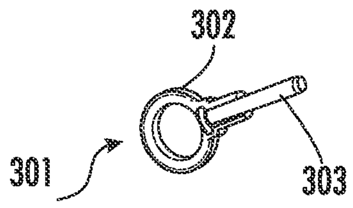
FIG. 4 is a perspective view a coupling device for removably attaching the alarm device of FIG. 3A to a suction cannister.

FIG. 4 illustrates an exemplary embodiment of a coupling device 301 for removably attaching device 100 to suction cannister 240. In this embodiment, coupling device 301 allows main body 200 of device 100 to engage with the top surface of suction cannister 240. Coupling device 301 includes a fastener for retaining device 100 to suction cannister 240. In certain embodiments, the fastener is a pin 303 which may further comprise a quick-release push-button along its body. Once pin 303 is inserted into opening 304, its exposed end may be further attached to a pin handle 302. Pin handle 302 facilitates fastening or releasing device 100 to or from suction cannister 240.

In certain aspects, projection 244 of the suction cannister 240 is a tab which has opening 245. For example, the top surface of each of first and second suction cannisters 240 comprises a protruding tab with an opening 245 that allows for the insertion of a fastener. However, it is understood that the surface of the suction cannister may comprise a different structure. For example, suction cannister 240 may not have projection 244 and the coupling may be accomplished using something other than pin 303 or other type of fastener. For example, other types of connections may removably attach main body 200 to suction cannister 240. In one aspect, a clamp may be placed around the body or neck of suction cannister 240. The clasping end of the clamp may secure suction cannister 240 in place while the other end of the clamp may be attached to or inserted through main body 200 of device 100. In such aspects, the coupling of suction cannister 240 to portable alarm device 100 would be accomplished using something similar to pronged extension clamps that hold chemical flasks in place.

In a preferred embodiment, device 100 includes a coupling device 301 on each opposing end 350 for attaching device 100 to two separate suction cannisters 240. Main body 200 of device is configured such that the patient may grasp and carry device 100 with two suction canisters about the room or halls of the hospital without disrupting the suction pressure applied to bypass device 10.

Figure 5:
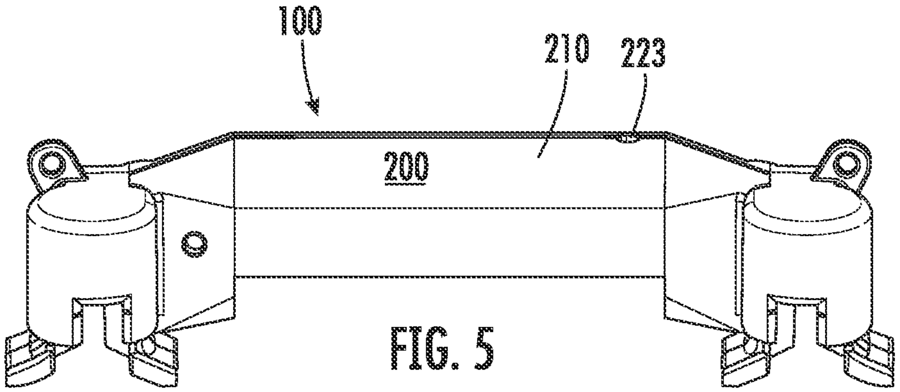
FIG. 5 is a perspective view of a main body of the portable alarm device of FIG. 3A.

FIG. 5 is a perspective view of main body 200 of alarm device 100. As previously mentioned, a length of about 6 inches of elongated portion 210 or main body 200 would result in a lighter weight system and would accommodate connections to smaller, low-volume canisters. Such systems may perhaps be used for young patients or those with small hands. Alternatively, a rigid main body 200 or elongated portion 210 having a length in the range of about 6 to 10 inches provides an easily maneuverable three-dimensional object with sufficient space for the average-sized patient's grip, giving the patient the ability to balance and control two suction cannisters. Alternatively, a device length above 15 inches would accommodate connecting to two canisters that are very large and may perhaps each have a diameter of greater than 6 inches, for example. It is understood that these device lengths are only examples of device lengths and the device's main body 200 may be longer or shorter than described herein.

In an exemplary embodiment, an LED illumination window 223 can be seen which allows an LED unit 220 (see FIG. 6) to shine light therethrough a signal that pressure from within the canister has reached a threshold value. In other embodiments, the signal comprises an audible alert. In other embodiments, the signal comprises both an audible and a visual alert. In yet other embodiments, the signal comprises data transmitted to a remote location. The signal may also be a combination of one or more types of alerts. Regardless of the alert type, the signal indicates that there has been a loss of negative pressure within the system, which may cause bypass device 10 to migrate or become less secure to the intestinal walls of the patient.

Figure 6:
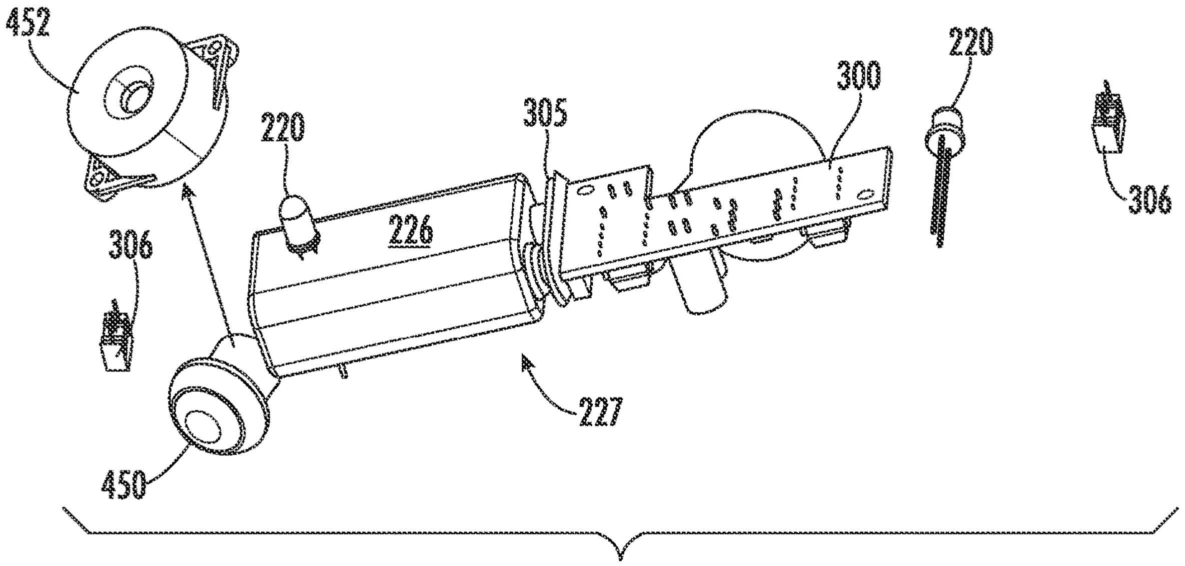
FIG. 6 is an exploded view of a signal device of the portable alarm device of FIG. 3A.

FIG. 6 is an exploded view of an embodiment of an exemplary signal device 227 for providing an alert that there has been a loss in suction pressure in the system. In certain embodiments, signal device 227 comprises an electronics assembly which includes a power supply 226, such as a battery, coupled to a circuit board 300 via a suitable connector 305. If device 100 is configured to emit an audible signal, then a buzzer 452 is present, shown in the exploded view as a component behind or internal to a mute button 450 that silences buzzer 452. The surface of mute button 450 is accessible to the patient or user for silencing the alarm. It is understood that other types of silencers and buzzers, including micro-buzzers, may be used in device 100.

In some embodiments, there may be two LED units 220, a mute button 450, and a buzzer 452. It is understood that components of signal device 227 may be configured in multiple different ways. For example, a power supply 226 may be disposed external to main body 200 of alarm device 100. The battery of power supply 226 may be a small, rechargeable battery and circuit board 300 may be shaped so as to fit power supply 226 and accompanying electronics within another section of the device 100. For example, power supply 226 may be housed within opposing end 350 of FIG. 2*a*. Device 100 may further have hardware for transmitting and receiving a Wi-Fi signal. It is understood that the components of signal device 227 and other electronics and adaptors may vary, and the disclosure herein is not limited to those embodied by FIG. 6.

In use, bypass device 10 is introduced endoscopically through the patient's rectum and into the large intestines 400, and then advanced to the anastomosis site 402. Stent 14 is expanded through any suitable manner known in the art and suction tubes 16, 18 are coupled to one or more suction cannisters 240 via medical tubing 340. Suction pressure is then applied to sheath 12 via suction tubes 16, 18 (see FIG. 1) to secure device 10 against the intestinal tissue. Device 10 is now properly placed to provide an internal bypass of intestinal contents such that these contents do not contact the anastomosis site, or leak through the anastomosis. A more complete description of the method of inserting device 10 into the patient is described in U.S. Pat. No. 9,339,272, previously incorporated herein by reference.

Portable alarm device 100 is coupled to each suction cannisters 240 by sliding projection 244 into base 352 such that protruding feet 353 are seated on the surface of the canister. In these embodiments, it is important that opening 245 of projection 244 aligns with open space 304 within the base 352. In this manner, pin 303 may be inserted through both openings and click into place when the quick-release button on its end reaches the housing space within opposing end 350 of device 100.

In a preferred embodiment, main body 200 and suction cannisters 240 are positioned by coupling device 301 such that element 307 of the tactile sensor is contactable by expandable element 243 of suction cannister 240 once pressure within the canister reaches a threshold value. Coupling device 301 is a unique and simple design that allows reproducibility in the precise configuration of suction cannisters 240 coupled to device 100. The coupling mechanism is also inherently lightweight and thus, does not further burden the patient.

If the pressure reaches a threshold value within the negative pressure system, element 243 expands, contacting element 307 of sensor 306 and signals the alarm as described above. This immediately alerts the patient or a healthcare practitioner that suction pressure has been lost and the system must be diagnosed or replaced to ensure that bypass device remains securely in place at the anastomosis site.

The devices in the present disclosure provide an easily graspable and lightweight design to enhance movement of the patient for personal needs or for performing exercises, such as for physical therapy. This allows the patient to be mobile during the recovery period, improving overall quality of life during the entire recovery window.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications, and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. An internal bypass system for a target site in a gastrointestinal (GI) tract of a patient for protecting an anastomosis in the GI tract, the bypass system comprising:

an anchor comprising a stent configured to be positioned within the GI tract of the patient at the target site upstream of the anastomosis, a flexible sheath coupled to the stent and having a length selected to extend from the target site and through the GI tract across the anastomosis to a location external to the patient, and at least one suction tube having a free end extending from the anchor and along the flexible sheath to the location external to the patient, the stent formed by a metal wire mesh having an outer wall configured to contact the GI tract's walls, the flexible sheath defining an internal channel; and a portable alarm device configured to be removably coupled to the free end of the at least one suction tube, the portable alarm device comprising:

a negative pressure system having a source of negative pressure configured to be fluidly coupled to the anchor via the at least one suction tube, the negative pressure system configured to create a vacuum at the anchor at the target site upstream of the anastomosis to suction the GI tract's walls against the outer wall of the metal wire mesh to thereby cause the anchor to remain in place throughout a healing period such that feces and other waste matter traveling though the GI tract will pass through the internal channel without contacting the GI tract's walls around the anastomosis;

a trigger configured to detect a pressure from within the negative pressure system provided by the source of negative pressure when the source of negative pressure is fluidly coupled to the anchor; and a signal device coupled to the trigger and configured to automatically emit a signal when the pressure reaches a predetermined threshold value indicating the negative pressure system suffering a loss in suction pressure that secures the anchor to the GI tract's walls at the target site upstream of the anastomosis.

2. The bypass system of claim 1, wherein the stent is configured to provide an outward radial force to the flexible sheath.

3. The bypass system of claim 1, wherein the source of negative pressure comprises:

at least one suction canister fluidly coupled to the at least one suction tube.

4. The bypass system of claim 3, wherein the main body comprises a coupling device for removably attaching the main body to the at least one suction canister.

5. The bypass system of claim 4, wherein the coupling device comprises a fastener sized to pass through an opening of the at least one suction canister and an opening of the main body.

6. The bypass system of claim 4, wherein the trigger comprises a movable element coupled to an outer wall of the at least one suction canister, the movable element being configured to move from a first position to a second position when a pressure of the at least one suction canister reaches a threshold level.

7. The bypass system of claim 6, further comprising a tactile sensor having a contact surface configured to contact a surface of the movable element in the second position when the main body is coupled to the at least one suction canister.

8. The bypass system of claim 7, wherein the tactile sensor is positioned such that the movable element contacts the tactile sensor when the pressure reaches the threshold level.

9. The bypass system of claim 8, wherein the tactile sensor is coupled to the signal device and configured to activate the signal device when the movable element contacts the tactile sensor.

10. The bypass system of claim 6, wherein the movable element comprises an expandable element coupled to the outer wall of the suction canister, the expandable element being configured to expand from the first position to the second position when the pressure of the suction canister reaches the threshold level.

11. The bypass system of claim 10, further comprising a tactile sensor having a contact surface configured to contact a surface of the expandable element of the suction canister when the main body is coupled to the suction canister.

12. The bypass system of claim 11, wherein the tactile sensor is positioned such that the expandable element contacts the tactile sensor when the pressure reaches the threshold level.

13. The bypass system of claim 4, wherein the at least one suction canister comprises a first suction canister and a second suction canister fluidly coupled to the at least one suction tube, and wherein the trigger comprises a first trigger and a second trigger, the first trigger configured to detect pressure within the first suction canister, the second trigger configured to detect pressure within the second suction canister.

14. The bypass system of claim 13, wherein the main body comprises an elongate body having first and second opposing ends, the first and second opposing ends each comprising a coupling device for coupling the main body to the first and second suction canisters.

15. The bypass system of claim 14, wherein the elongate body comprises a handle for grasping and carrying the main body and the first and second suction canisters.

16. The bypass system of claim 14, wherein the coupling device of the first and second opposing ends is configured for removably coupling to the first and second suction canisters, respectively.

17. The bypass system of claim 1, wherein the signal comprises an audible alert.

18. The bypass system of claim 1, wherein the signal comprises a visual alert.

19. The bypass system of claim 1, wherein the signal comprises data and the signal device further comprises a transmitter for transmitting the data to a remote location.

20. A method for monitoring an internal bypass system positioned at a target site in a gastrointestinal (GI) tract of a patient for protecting an anastomosis in the GI tract, the method comprising:

positioning an anchor comprising a stent within the GI tract of the patient at the target site upstream of the anastomosis such that a flexible sheath coupled to the stent has a length that extends from the target site and through the GI tract across the anastomosis to a location external to the patient, and at least one suction tube having a free end extends from the anchor and along the flexible sheath to the location external to the patient, the stent formed by a metal wire mesh having an outer wall configured to contact the GI tract's walls, the flexible sheath defining an internal channel;

removably coupling a source of negative pressure of a negative pressure system disposed within a portable alarm device to the free end of the at least one suction tube to fluidly couple the anchor to the source of negative pressure;

creating a vacuum at the anchor at the target site upstream of the anastomosis via the at least one suction tube using the negative pressure system to suction the GI tract's walls against the outer wall of the metal wire mesh to thereby cause the anchor to remain in place throughout a healing period such that feces and other waste matter traveling though the GI tract will pass through the internal channel without contacting the GI tract's walls around the anastomosis;

detecting, via a trigger of the portable alarm device, a pressure from within the negative pressure system provided by the source of negative pressure when the source of negative pressure is fluidly coupled to the anchor; and automatically emitting a signal when the pressure reaches a predetermined threshold value indicating the negative pressure system suffering a loss in suction pressure that secures the anchor to the GI tract's walls at the target site upstream of the anastomosis.

21. The method of claim 20, wherein emitting the signal responsive to detecting the negative pressure system suffering the loss in suction pressure comprises emitting an audible or visual alert.

* * * * *